United States Patent [19]

Suzuki et al.

[11] Patent Number: 4,504,773
[45] Date of Patent: Mar. 12, 1985

[54] CAPACITOR DISCHARGE CIRCUIT

[75] Inventors: Seiichi Suzuki, Fukushima; Eihachiro Tomita, Kanagawa, both of Japan

[73] Assignees: Kureha Kagaku Kogyo Kabushiki Kaisha; Radio Research Technical, Inc., both of Tokyo, Japan

[21] Appl. No.: 415,831

[22] Filed: Sep. 8, 1982

[30] Foreign Application Priority Data

Sep. 10, 1981 [JP] Japan .................. 56-142832

[51] Int. Cl.³ .................................... H02J 7/00
[52] U.S. Cl. ................................ 320/1; 361/3; 128/419 D
[58] Field of Search ........ 128/419 PG, 419 D, 419 S; 307/137, 141; 320/1; 361/2, 3, 5, 6, 13

[56] References Cited

U.S. PATENT DOCUMENTS

| 3,440,445 | 4/1969 | Kusa | 361/3 X |
| 4,001,610 | 1/1977 | Griffin | 320/1 X |

FOREIGN PATENT DOCUMENTS

| 1256638 | 12/1971 | United Kingdom . |
| 1343256 | 1/1973 | United Kingdom . |
| 1443324 | 7/1976 | United Kingdom . |
| 211028 | 5/1968 | U.S.S.R. | 128/419 D |

OTHER PUBLICATIONS

Medical Instrument Magazine, vol. 38.5 (1968), pp. 304–307, and 314–315.
Thyristor Application Circuit Technology (1976), pp. 1–5 and 140–141.
Hitach Review, vol. 63, No. 6 (1981), pp. 5–10.

Primary Examiner—William H. Beha, Jr.
Assistant Examiner—Anita M. Ault
Attorney, Agent, or Firm—Woodcock, Washburn, Kurtz, Mackiewicz & Norris

[57] ABSTRACT

A capacitor discharge circuit constructed by a combination of a mechanical switch and an electronic switch. The electronic switch is automatically turned on with a predetermined time delay after closing of the mechanical switch. The mechanical switch is used to completely separate a high voltage-large capacity capacitor from a load when the discharge operation is not required. The wear and tear of contacts in the mechanical switch can be avoided by the delayed operation of the electronic switch.

8 Claims, 5 Drawing Figures

FIG. I
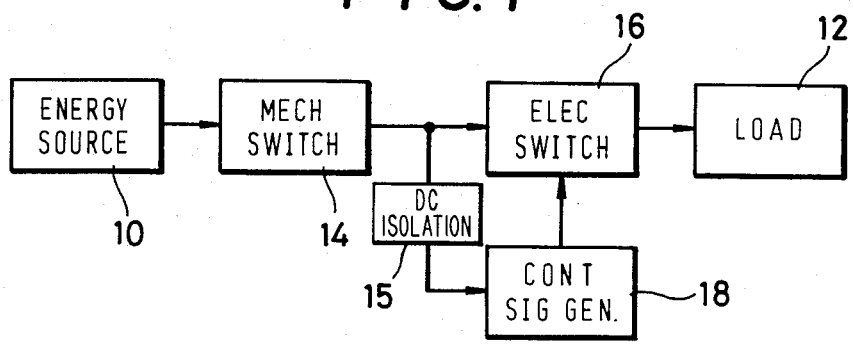
FIG. 2
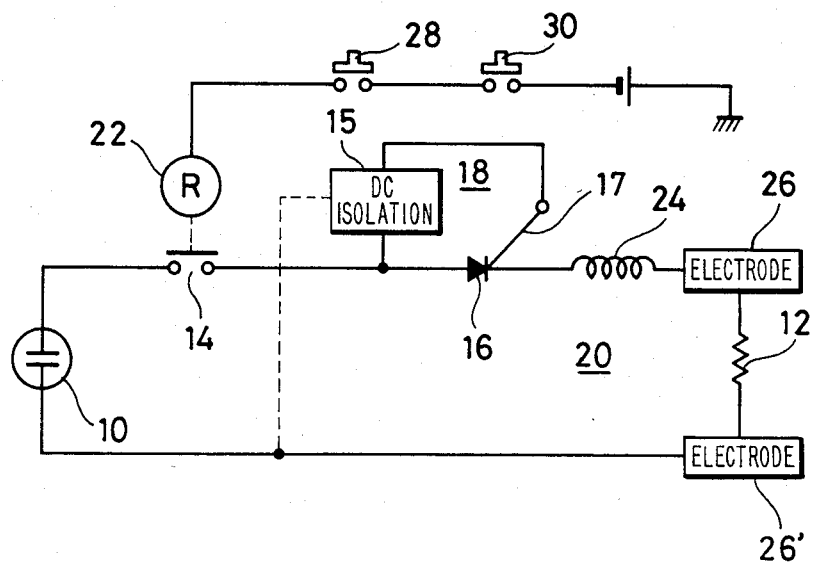
FIG. 3
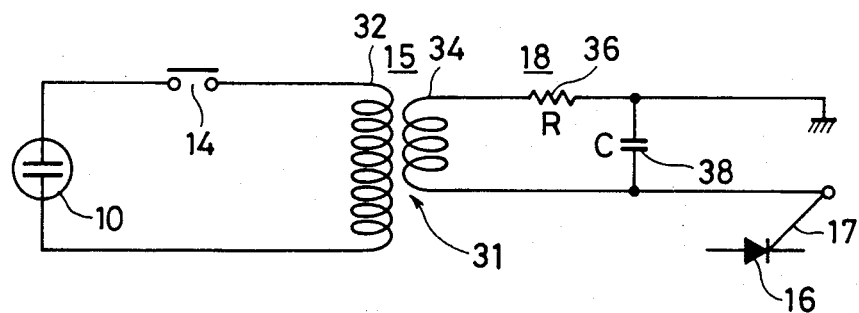

CAPACITOR DISCHARGE CIRCUIT

BACKGROUND OF THE INVENTION

1. Field of the invention

This invention relates to a capacitor discharge circuit in general and particularly to a discharge circuit constructed by a combination of a mechanical switch and an electronic switch and used for discharging a high voltage-large capacity capacitor.

2. Description of the Prior Art

In recent years, it has been reported that the demand for an extremely small apparatus including a high voltage-large capacity capacitor and capable of being carried by hands is increasing year by year. Among such apparatuses, there are a defibrillator (or resuscitator) for emergency use, a machine tool using a laser, a medical instrument and the other type of apparatus which includes a high voltage-large capacity capacitor and utilizes the instantaneous discharge of a large amount of electric charge from the capacitor.

An oil-sealed type switch has been customarily used as a switch for instantaneously discharging a comparatively large amount of electric charge, but it is not suitable for use as portable type because of such drawbacks as it becomes rether heavy due to the weight of oil and a container thereof, and the oil is liable to drop out of the container due to vibration. On the contrary, an air-open type switch is light in weight, but has disadvantages that arc discharge occurs violently at the time of on-off operation and the wear and tear of contacts is remarkable. A silicon controlled rectifier or thyristor is well known as an electronic switch which is not accompanied with any arc discharge at the time of on-off operation, but some amount of leakage currents may exist even when it is not conducting. Assuming now that the thyristor is used, by itself, as a switch for a capacitor discharge circuit in the defibrillator, for example, it may often lead to very serious accidents. The defibrillator is a device which applies the current at high voltages from the capacitor to the heart of human being in a syncopic state for a short period of time in order to bring him back to consciousness, so that the leakage current through the thyristor, if any, is dangerous since the electric charge from the capacitor may be storaged between both electrodes even when the circuit is not in use.

SUMMARY OF THE INVENTION

It is therefore an primary object of the present invention to provide a capacitor discharge circuit which can not only avoid the wear and tear of a contact due to the generation of sparks at the time of discharge, but also be completely cut off without leadage.

The aforesaid object in accordance with the present invention can be accomplished by inserting a mechanical switch and an electronic switch, in series, in a discharge line for a capacitor so that the former is located at the capacitor side, and providing a control signal generation circuit connected to the line between these two switches through an isolator. The electronic switch will be turned on with a predetermined time delay after closing of the mechanical switch, so that the generation of sparks at the time of operation of the mechanical switch can be substantially prevented. And, the application of electricity to a human body when not in use can be completely avoided by means of the mechanical switch.

BRIEF DESCRIPTION OF THE DRAWINGS

The above and other objects, features and advantages of the present invention will be apparent from the following detailed description in conjunction with the accompaning drawings illustrating its preferred embodiment, wherein like reference numerals refer to like elements or parts, and in which:

FIG. 1 shows a block diagram for the capacitor discharge device in accordance with the present invention;

FIG. 2 shows a circuit diagram of a defibrillator incorporating a high voltage-large capacity capacitor, illustrating a concrete example of the capacitor discharge circuit of FIG. 1;

FIG. 3 shows a concrete circuit diagram illustrating a control signal generation circuit used in FIG. 2;

DESCRIPTION OF THE PREFERRED EMBODIMENT

Figure 4:
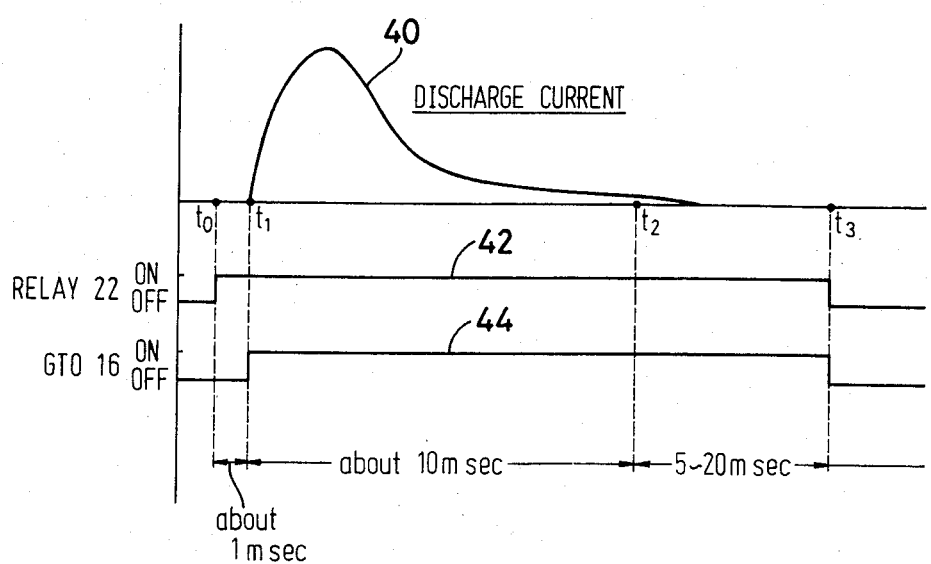
FIG. 4 shows a discharge current curve obtained by the circuit in FIG. 2 and a time chart for the operation of the circuit.
Figure 5:
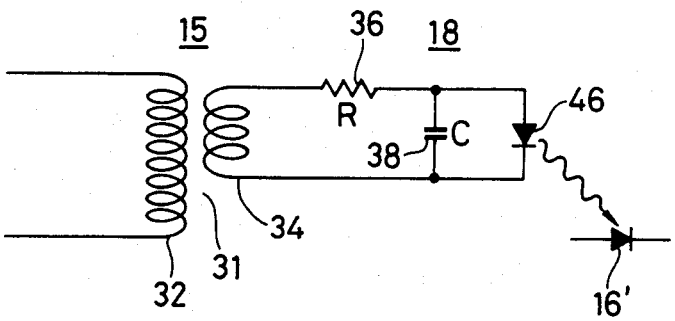
FIG. 5 shows another embodiment of a isolator.

Referring now to FIG. 1 which illustrates a block diagram for the capacitor dischage circuit in accordance with the present invention, an energy source 10 is connected to a load 12 through a mechanical switch 14 and an electronic switch 16 inserted in series therebetween. There is provided a control signal generation circuit 18 connected to the line between the switches 14 and 16 through an isolator 15 for forming an actuation signal or turn-on signal to the electronic switch 16. The control signal generation circuit 18 functions to provide a control signal to the electronic switch 16 to turn it on with a predetermined time delay after closing of the mechanical switch 14. In addition, the mechanical switch 14 is also used to completely isolate the load 12 from the energy source 10 when the operation of the circuit is being interrupted.

Referring to FIG. 2 which is a circuit diagram of defibrillator incorporating a high voltage-large capacity capacitor, illustrating a concrete example of the capacitor discharge circuit of FIG. 1, the energy source 10 in FIG. 1 is represented by a capacitor. An electromagnetic relay 22 is used as the mechanical switch 14 of FIG. 1 in the output circuit 20 for the capacitor 10. A gate turn off thyristor (hereinafter referred to as GTO or thyristor) is used as the electronic switch 16. The contact 14 of the electromagnetic relay 22 and the thyristor 16 are connected in series, and an inductance coil 24 and a pair of electrodes 26, 26' are disposed at the load side thereof. A human body (indicated by a load resistor 12) in a syncoptic state is connected across the electrodes 26, 26' as the load 12 in FIG. 1. The control signal generation circuit 18 branched from the line between the contact 14 of the relay 22 and the GTO 16 is connected to the gate 17 of the GTO via the isolator 15. The relay 22 is operated by two pushbutton switches 28 and 30.

Referring to FIG. 3 which is a circuit diagram illustrating one example of the control signal generation circuit 18 used in FIG. 2. A transformer type device is used as the isolator 15, and the primary coil 32 of the transformer 31 is connected to both ends of the capacitor 10 through the relay contact 14. A low voltage induced on the secondary coil 32 of the transformer 31 is applied as gate signal to the gate 17 of the GTO 16 through a delay circuit comprising a resistor 36 and a capacitor 38. In operation, when the pushbutton switches 28 and 30 are depressed, the reley 22 is energized to close the contact 14. At this stage, there is no spark from the contact 14 since the circuit of GTO 16 is off. Simultaneously with this, the voltage on the capacitor 15 is applied to the isolator 15. With the relay 22 on, a high voltage (4 to 5 KV, for example) of the capacitor 10 is applied to the primary coil 32 of the isolator 15. A pulse due to a shock at this instant is induced at the secondary coil 34, and a low voltage on the order of several volts determined by the isolator reaches the gate 17 of the GTO 16 to turn on the circuit of the GTO 16. Since the delay circuit consisting of the resistor 36 and the capacitor 38 is disposed as shown in the drawing, the voltage induced on the secondary coil is applied to the gate with a time delay T determined by T=CR, where R represents a resistance of the resistor 36 and C represents a capacitance of the capacitor 38. By choosing "T" appropriately, the generation of sparks can be completely avoided even when the on-off of the contact 14 is repeated for a short period of time due to a chattering of the relay 22. As the isolator, it is not restricted to such transformer type as shown in FIG. 3, but any type of device wherein the high voltage at the primary side can be supplied to the gate 17 of GTO as isolated low voltage current can be used as well. As the isolator of this kind, there are a sound wave propagation type device, photoelectric type and other optional ones, for example.

With the GTO 16 turned on, a high voltage current of large energy (200 to 400 joules, 60 to 75 A, peak voltage: 2000 to 4500 V, for example) flows into the human body 12, and due to the shock at this instant, the human being in a syncopic state can be brought back to conciousness.

The timing of circuit operation will be explained in detail by referring to the discharge current curve and the time chart in FIG. 4. In the drawing, a horizontal axis represents a time elapsed, a curve 40 represents a discharge current flowing to the resistor 12, a time chart 42 is for the electromagnetic relay 22, and a time chart 44 is for the GTO 16. The contact 14 of relay 22 goes on at time $t_0$ by manually depressing the push button switches 28, 30 and the GTO 16 is turned on at $t_1$. The time difference indicated by $t_1 - t_0$ corresponds to the delay time (usually, 1 to 2 msec) determined by the delay elements 36 and 38 and is a time interval during which no current flows through the contact 14 in a substatial sense, so that it insures that the contact 14 can be closed without sparks.

Although the GTO is turned on at time $t_1$ and the discharge of the condenser is started, the smooth switching without chattering will be made since the thyristor switch is a contactless device. The energy of more than 95% of the total stored in the capacitor will be discharged within approx. 10 msec, and the current energy flowing through the circuit 20 will become very low at time $t_2$. The handling time for the pushbutton switch differs from person to person, or depending on the method of handling, but it usually takes 15 to 30 msec when the two pushbuttons 28 and 30 are depressed by both thumbs of the operator as in the case of the defibrillator. Therefore, the energy at the moment $t_3$ when the pushbutton is released and the contact of the relay 22 is disconnected, becomes even lower and there is no spark due to the release of the contact in a substatial sense. With the relay cut and the circuit current breaked completely, the GTO 16 is spontaneously returned to its off state.

In FIGS. 2 to 3, it is assumed that the GTO is used as thyristor, but any type of thyristor other than the GTO can be operated almost equally since the cutting-off for the circuit current will be made by means of the relay.

Referring to FIG. 4 which illustrates another embodiment of the control signal generation circuit 18 in FIG. 3, a control signal generation circuit 18 in this embodiment comprises a light emitting diode 46, in addition to the transformer 31, resistor 36 and capacitor 38. In this case, a photo trigger thyristor 16' with a light-sensitive gate thereof may be used instead of the GTO thyristor 16. A light signal corresponding to the delayed control signal can be lead to the light-sensitive gate of the thyristor 16' through an appropriate optical fiber.

As clearly understood from the foregoing, the operation and effect attained by this invention further includes the followings in addtion to the matters mentioned previously. Since the low voltage for triggering the gate of the thyristor is obtainable by lowering the high voltage from the capacitor via the step-down transformer, an independent low voltage source is not purposely required. In addtion, the start and stop of the thyristor is associated with the operation of the mechanical switch, so that the switching operation of the circuit will be greatly simplified.

While the capacitor discharge circuit of the present invention has been described in conjunction with an application to defibrillators, the invention is by no means limited thereto, and it will be obvious to those skilled in the art that numerous changes and modification may be made without departing from the spirit and scope of the invention.

For example, such changes as a laser is used as load, a sound wave propagation type device is used as control signal generation circuit, a manual knife switch is used instead of a relay, and extension of a delay time for the case where a comparatively long chattering operation can not be avoided are cases in points.

What is claimed:

1. A capacitor discharge circuit for a defibrillator comprising:
   a mechanical switch having mechanical make-contact connected to the output of a capacitor which is charged by a DC high voltage source;
   an electronic switch connected in series to the output of the mechanical switch, the output of said electronic switch being connected to a load;
   a control signal generation circuit for generating a turn-on signal to be supplied to a control input of said electronic switch, said control signal generation circuit being connected to the output of said mechanical switch; and
   a DC isolating means for feeding a reduced operation voltage from the output of said mechanical switch to said control signal generation circuit with electrical isolation therebetween, wherein said control signal generation circuit is operated when said mechanical switch is turned on, and said electronic switch is turned on in turn in response to said turn-on signal generated in said control signal generation circuit.

2. A capacitor discharge circuit for a defibrillator comprising:

a mechanical switch having mechanical make-contact connected to the output of a capacitor which is charged by a DC high voltage source;

an electronic switch connected in series to the output of the mechanical switch, the output of said electronic switch being connected to a load;

a control signal generation circuit for generating a turn-on signal to be supplied to a control input of said electronic switch, said control signal generation circuit being connected to the output of said mechanical switch;

a DC isolating means for feeding a reduced operation voltage from the output of said mechanical switch to said control signal generation circuit with electrical isolation therebetween; and a delay circuit for delaying said turn-on signal, the delay time of said delay circuit being a period longer than the chattering operation period of said mechanical switch; wherein said control signal generation circuit is operated when said mechanical switch is turned on, and said electronic switch is turned on after the chattering operation period is over in response to said turn-on signal generated in said control signal generation circuit and delayed by said delay circuit.

3. A capacitor discharge circuit according to claim 1 or 2, wherein the output of said electronic switch is directed to an electrode of said defibrillator.

4. The capacitor discharge circuit according to claim 1 or 2, wherein said mechanical switch means is an electromagnetic relay.

5. A capacitor discharge circuit according to claim 4, said relay comprises a pair of manually operated switches connected in series with each other, said manually operated switches being connected to an energizing circuit of said relay.

6. The capacitor discharge circuit according to claim 1 or 2, wherein said electronic switch means is a gate turn-off thyristor.

7. A capacitor discharge circuit according to claim 2, wherein said isolating means is a transformer having a primary winding connected to the output of said mechanical switch and a secondary winding for supplying a low voltage to said control signal generation circuit, and said delay circuit is a time-constant circuit comprising a resistor and a capacitor connected in series to said secondary winding of said transformer, an output of said time-constant circuit being fed to said electronic switch as said turn-on signal.

8. A capacitor discharge circuit according to claim 1 or 2 wherein said electronic switch is a light triggering type thyristor having a light sensitive gate, and said control signal generation circuit comprises a light emitting diode for generating a light to said light triggering thyristor as said turn-on signal.

* * * * *